United States Patent [19]
Bernstein

[11] Patent Number: 5,478,334
[45] Date of Patent: Dec. 26, 1995

[54] URINE COLLECTING ASSEMBLY FOR INCONTINENT MALES

[76] Inventor: Jerry Bernstein, 317 W. 89th St., Suite 7W, New York, N.Y. 10024

[21] Appl. No.: 268,332

[22] Filed: Jun. 30, 1994

[51] Int. Cl.$^6$ ..................................................... A61F 5/44
[52] U.S. Cl. ......................... 604/353; 604/349; 604/345
[58] Field of Search ................................ 604/332, 335, 604/345, 349–353; 4/144.1–144.4

[56] References Cited

U.S. PATENT DOCUMENTS

| | | | |
|---|---|---|---|
| 2,496,175 | 1/1950 | Perry | 604/335 |
| 2,778,362 | 1/1957 | Pollock et al. | 604/345 |
| 5,330,455 | 7/1994 | McKay | 604/345 |
| 5,342,332 | 8/1994 | Wheeler | 604/349 |

FOREIGN PATENT DOCUMENTS

| | | | |
|---|---|---|---|
| 0161047 | 11/1985 | European Pat. Off. | 604/353 |
| 0674158 | 4/1939 | Germany | 604/349 |
| 2206050 | 12/1988 | United Kingdom | 604/349 |
| 2233232 | 1/1991 | United Kingdom | 604/349 |

*Primary Examiner*—Randall L. Green
*Assistant Examiner*—Rob Clarke
*Attorney, Agent, or Firm*—Michael Ebert

[57] ABSTRACT

A urine collecting assembly installable on an incontinent male, the assembly including a normally-flat urostomy pouch having a lateral inlet adjacent its upper end bordered by a circular belt-adapter flange, whereby the pouch may be strapped onto the hips or waist of an incontinent male whose penis then projects toward the inlet. The pouch is combined with a complementary circular fixture which is fitted over the penis and then snapped onto the flange of the pouch. Mounted on the fixture is an open-ended short condom, the rear end of which is stretched and attached to the fixture, the open front end of the condom then snugly engaging the shaft of the penis from whose head urine is discharged into the pouch through its inlet. The condom functions as a sealing membrane to prevent urine backup so that the incontinent male is not soiled by his own urine.

11 Claims, 2 Drawing Sheets

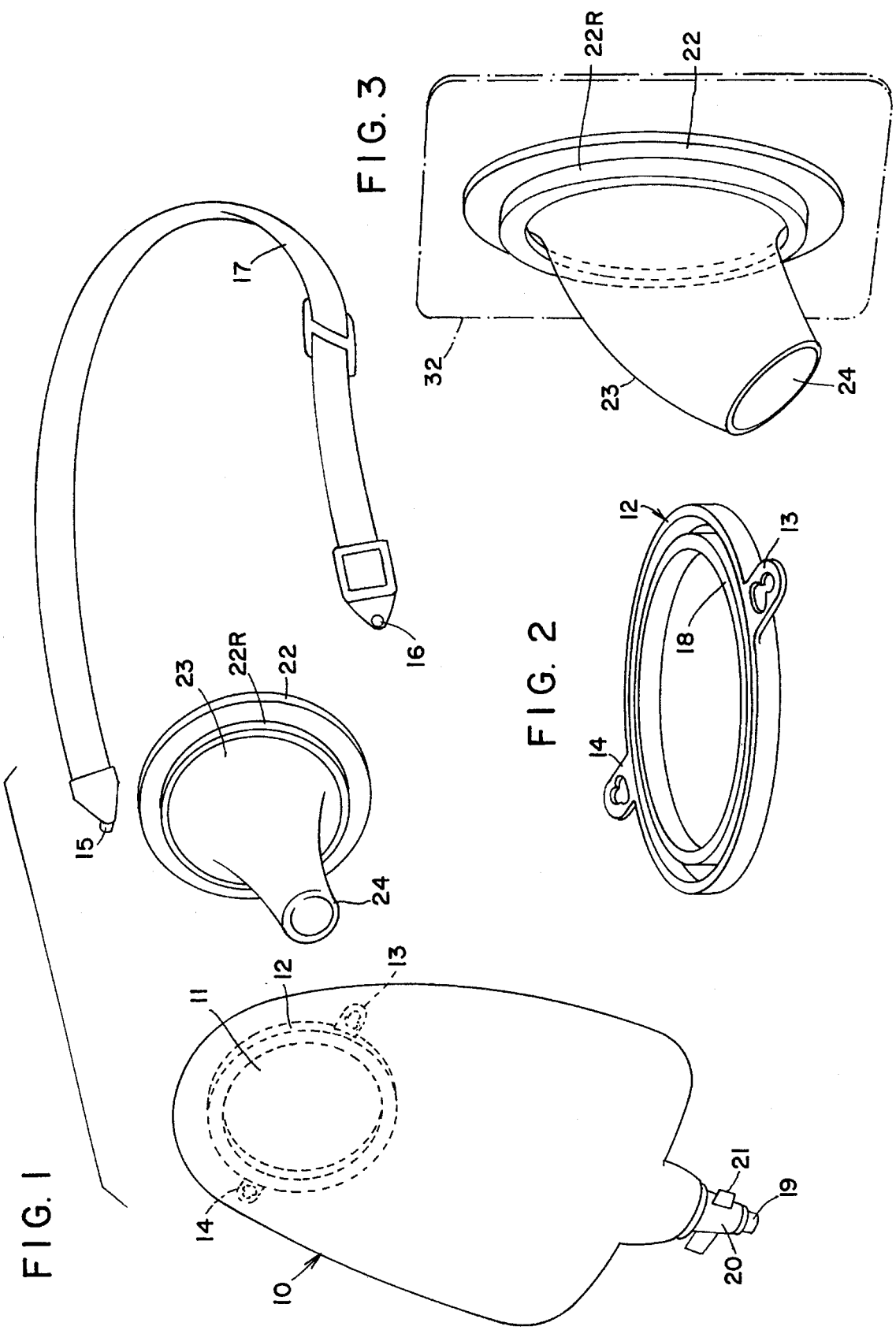

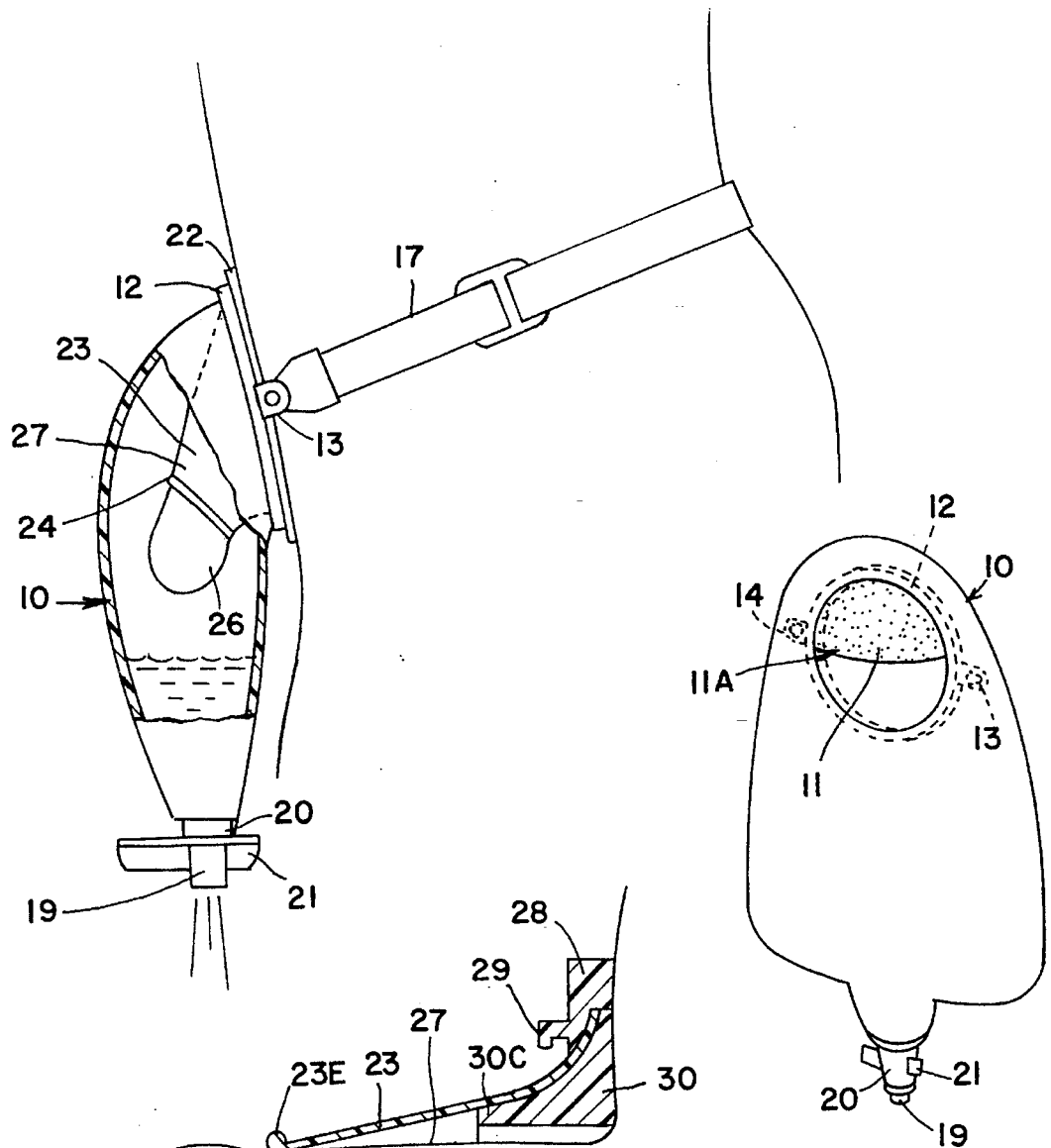
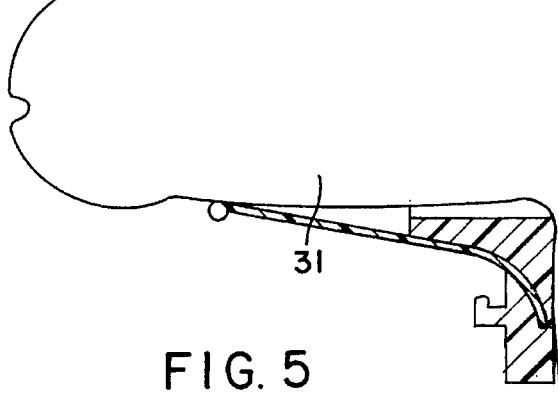
FIG. 4
FIG. 6
FIG. 5

URINE COLLECTING ASSEMBLY FOR INCONTINENT MALES

BACKGROUND OF INVENTION

1. Field of Invention

This invention relates generally to urine drainage devices for incontinent males, and more particularly to a urine collecting assembly that includes a urostomy pouch that is normally flat and is adapted to be strapped onto the hips or waist of an incontinent male to collect urine discharged from his penis and to prevent the backup of urine so that the male is not soiled by his own urine.

2. Status of Prior Art

With advanced age, many men become incontinent and lose the ability to control the flow of urine from their bladder. This may occur not only in geriatric males but also in those who are chronically ill or suffer from nerve damage and other disorders which impair a man's ability to control the discharge of urine. But regardless of the cause of incontinence, this condition may give rise to emotional, social and psychological problems. Thus the use of oversize diapers in nursing homes for elderly males is a poor solution, for incontinent males often spend hours seated in drenched diapers.

Various devices have heretofore been devised to reduce or eliminate the embarrassment and social stigma associated with the loss of bladder control, and to make it possible for incontinent men to lead nearly normal lives. One known device for this purpose takes the form of an external catheter constituted by a tight-fitting condom whose normally-closed end is provided with a plastic connector fastened to a plastic bag strapped to the calf of the incontinent male to collect urine discharged from the penis. A catheter system of this type, as noted in the Jensen et al. U.S. Pat. No. 4,673,401, is unconfortable to wear and in certain circumstances, such as where the penis is very small or shriveled, is incapable of containing the urine discharged therefrom, for the condom is then unable to hold tightly to the penis.

Where the catheter takes the form of a tight fitting condom, it often entraps pubic hair surrounding the male organ, making it necessary to shave this hair to avoid pain during use or removal of the catheter. Such catheter condoms are frequently coated internally with an adhesive which makes removal both difficult and painful.

The Jensen et al. patent discloses a urine collector for an incontinent male in the form of a receptacle detachably mounted on a brief or undergarment worn by the male. The receptacle has a penis-receiving opening defined by a rigid ring that engages a complementary piece on the wall of the brief. A flexible membrane engages the penis to prevent urine backup into the brief.

The patent to Appelbaum U.S. Pat. No. 3,526,227 discloses a urinal pouch extending from a support pouch having leg and waist straps to secure the device in place. The pouch includes an inner flexible open-ended sheath to provide sealing in conjunction with the male organ of the wearer. The U.S. Pat. No. 1,423,537 to Muller discloses a plate attached to a waistband, with a sleeve projecting from the plate to place the head of the penis within a bag.

Also of background interest in regard to urine collecting device for incontinent males are the various devices for this purpose disclosed in the Matsuura U.S. Pat. Nos. 4,838,883 and 4,886,510, as well as in the Hesterman et al. U.S. Pat. No. 3,721,243, the Denard U.S. Pat. No. 4,387,726, the Giacalone U.S. Pat. No. 4,568,340 and the Windom U.S. Pat. No. 3,684,424.

All of the above-cited prior patents have practical drawbacks, for either they are difficult to install on an incontinent male, or the cost of the device is relatively high, for these devices require specially-designed urine collection bags and associated equipment such as spouts, tubes and panels. Moreover these devices do not provide a satisfactory solution to the problem of urine backup.

SUMMARY OF INVENTION

In view of the foregoing, the main object of the invention is to provide a urine collecting assembly for incontinent males that acts to collect all urine discharged from the penis of the user, the assembly being easily installed and being comfortable to wear.

More particularly, an object of the invention is to provide a sanitary urine collecting assembly of the above-type which includes a standard low-cost, mass-produced, urostomy pouch as the urine collector, the overall cost of the assembly being determined largely by that of the pouch.

Also an object of the invention is to provide an assembly of the above type which is effective regardless of the size of the user's male organ, and which acts to collect all urine discharged from the organ and to prevent the backup of the collected urine so that the user is maintained in a clean, dry state and is not soiled by his own urine.

A significant advantage of the invention is that the standard urostomy pouch is provided with a drainage valve, hence it is not necessary, when the pouch is loaded with urine, to detach the pouch from the assembly, for the pouch may be readily drained without disturbing the installation.

Yet another object of the invention is to provide an assembly that includes a guard that shields the pubic hair surrounding the penis and avoids the need to shave this hair which otherwise could give rise to discomfort when the assembly is installed, and it also avoids the use of adhesives.

Still another object of the invention is to provide a urine-collecting pouch whose inlet causes a penis projecting therein to aim downwardly to facilitate urine collection.

Briefly stated, these objects are attained by a urine collecting assembly installable on an incontinent male, the assembly including a normally-flat urostomy pouch having a lateral inlet adjacent its upper end bordered by a circular belt-adapter flange, whereby the pouch may be strapped onto the hips or waist of an incontinent male whose penis then projects toward the inlet. The pouch is combined with a complementary circular fixture which is fitted over the penis and then snapped onto the flange of the pouch. Mounted on the fixture is an open-ended short condom, the rear end of which is stretched and attached to the fixture, the open front end of the condom then snugly engaging the shaft of the penis from whose head urine is discharged into the pouch through its inlet. The condom functions as a sealing membrane to prevent urine backup so that the incontinent male is not soiled by his own urine.

BRIEF DESCRIPTION OF DRAWINGS

For a better understanding of the invention, as well as other objects thereof, reference is made to the following detailed description of the invention to be read in conjunction with the accompanying drawings in which:

FIG. 1 is an exploded view of the components which make up and assembly in accordance with the invention;

FIG. 2 is a perspective view of the belt-adapter flange that borders the inlet of the urostomy pouch included in the assembly;

FIG. 3 is a perspective view of the circular fixture included in the assembly;

FIG. 4 shows the assembly installed on an incontinent male;

FIG. 5 is a modified form of the fixture; and

FIG. 6 is a modified form of the pouch.

DETAILED DESCRIPTION OF INVENTION

Referring now to FIG. 1, a urine collecting assembly for an incontinent male which is effective regardless of the size of his penis, includes a standard, normally-flat urostomy pouch formed of superposed plies of transparent synthetic plastic film which are peripherally bonded to define a urine receptacle. The plastic for this purpose may be of polyethylene, polypropylene or other high-strength film material impervious to urine. Such low cost pouches are disposable.

A standard urostomy pouch is intended to receive urine discharged not from the penis of a male, but from an artificial opening or stoma produced by a urostomy procedure in which an opening from the urinary tract that includes the kidneys and uretha involved in the formation and secretion of urine is surgically constructed. A standard urostomy pouch is adapted to receive urine discharged from a surgically constructed stoma.

But in an assembly in accordance with the invention, a standard urostomy pouch or a specially-designed pouch is combined with a complementary fixture having mounted thereon an open-ended condom to function as a collector for urine discharged from the penis of an incontinent male and to prevent backup of the urine so that the incontinent male is not soiled by his own urine.

Standard pouch 10 is provided with a lateral inlet 11 or circular opening formed on one of its plastic plies adjacent the upper end of the pouch to admit urine into the normally flat pouch, the pouch being dilated by the urine collected therein. The bank of inlet 11 is bordered by a circular flange 12 molded of flexible synthetic plastic material of polyvinyl chloride or similar high-strength material which is impervious to urine. Flange 12 is provided with diametrically-opposed ears or links 13 and 14 to which are connectable the end connectors 15 and 16 of a belt 17 of adjustable length. Belt 17 which encircles the hips or waist of the incontinent male, acts to suspend the pouch in front of the penis, so that the penis projects toward the inlet.

As shown separately in FIG. 2, flange 12 is provided with an annular channel 18 defined by flexible walls, the channel being undercut so that when a complementary fixture having a circular ridge is snap-fitted into the channel, the fixture is locked to the flange and may be later detached therefrom when necessary. In practice, instead of a snap fit, locking may be effected by a partial turn of the fixture.

Pouch 10 includes at its lower end a drainage outlet 19 having a valve 20. Valve 20 is provided with an actuator arm 21, the valve being open to drain the urine when arm 21 is at right angles to the plane of the flat pouch, and being closed when the arm is parallel thereto. Hence when the pouch is loaded with urine, it is a simple matter to drain the urine therefrom into a container for disposal without having to remove the pouch from its installed position. Some urostomy pouches include a catch system to prevent collected urine from backing up to the upper section of the pouch.

In an assembly in accordance with the invention, pouch 10 is not coupled to a fixture surrounding a surgically-constructed stoma, but is joined to a complementary fixture 22 molded of flexible plastic material which is the same or similar to the material from which flange 12 is molded. Fixture 22, shown separately in FIG. 3 which goes on before the pouch, is provided with a raised circular ridge 22R which snaps into channel 18 of the pouch flange, thereby uniting the fixture with the flange.

Fixture 22 which fits over the penis of the incontinent male, has a circular opening whose diameter is greater than that of any penis regardless of its size; hence the fixture itself does not function as a seal. Mounted on fixture 22 is a short, open-ended condom 23 of latex or other elastomeric material whose rear end is stretched and attached to the fixture, the condom projecting forwardly from the fixture.

The open, normally rolled front end 24 of the condom 23 which has a small diameter is stretched when the male penis goes through the fixture and the condom projecting therefrom. The length of the condom is such when the open end thereof is unrolled, it then snugly engages the shaft of the penis whose head is then within the inlet 11 of the pouch 10 to discharge urine therein.

In practice, the normally-rolled front end of the condom may be fitted over a free collar to maintain an opening to receive the penis, and when the front end is unrolled to engage the shaft of the penis, the collar which fits loosely over the penis is then discarded.

The fixture is preferably adapted to cause the penis projecting through the condom mounted on the fixture to be downwardly inclined. One advantage of this penis inclination is that when the male is lying down, the urine then discharged from his penis will not back up.

In a preferred embodiment, the condom incorporates a web between the stretched rear end and a point on the condom which causes the condom to project downwardly from the fixture. Or the mounting of the condom on the fixture may be such that its open end which projects from the stretched rear end is not coaxial with the center of the fixture but is off axis so that it is closer to the lower end of the fixture to facilitate aiming the penis downward.

The design of the condom must take into account that in some instances incontinent males of advanced years have very small penises; hence the unstretched diameter of the open front end 24 of the penis must be even smaller so that the open end is stretchable to engage the shaft of the penis.

Thus as shown in FIG. 4 which illustrates how the assembly is strapped to the hips or waist 25 of an incontinent male, the penis of the male passes through fixture 22 coupled to the flange 12 of pouch 10, and projects into the inlet of the pouch so that the head 26 of the penis discharges urine into the pouch to be collected thereby. The front end 24 of condom 23 whose stretched rear end is attached to fixture 12, then snugly engages the shaft 27 of the penis.

As a consequence of this relationship, condom 23 then defines a sealing membrane which prevents a backup of urine, so that the incontinent male is not soaked by the urine he involuntarily discharges, all urine being collected by the pouch and no urine passing through the fixture.

It is a simple matter to install the assembly, for all that is necessary is to first fit fixture 22 over the penis of the male and to pull the condom over the penis going through fixture 12, the front end of the condom then being unrolled to snugly engage the shaft 27 of the penis. Then flange 12 of pouch 10 is joined to the fixture so that now the head 26 of the penis is within the pouch. Finally, belt 17 is applied to the hips or waist of the male and its end connectors 15 and 16 connected to links 13 and 14 on the flange, thereby completing the installation. When the pouch is suspended from the waist of the male, the fixture is held firmly in place.

The pouch is suspended from the waist belt so that it lies against the crotch of the male and is inconspicuous when the male is fully clothed. Hence the male may engage in normal activities without embarrassment, and when the pouch is loaded with urine, the male may open the fly of his trousers and pull out the drain of the pouch to drain the urine therefrom.

In order to make it possible to suspend the pouch so that it is angled to lie adjacent the right or left leg of the male, rather than over the crotch so that it is more comfortable to wear under trousers, some urostomy pouches, in addition to a pair of diametrically opposed ears or links on the flanges have a third or fourth link at a displaced position. Hence by attaching the belt connection to the first and a third or fourth link, the pouch will then be angled.

Modified Fixture

In order to provide better support for the condom 23 whose rear end is stretched and attached to the fixture which goes over the penis of the incontinent male, the fixture 28 shown in FIG. 5 which has a circular ridge 29 that snaps into the annular channel of the pouch flange, is provided with a molded plastic insert 30 terminating in a cylindrical collar 30C. Insert 30 has the form of a truncated cone that supports the stretched rear end of condom 23 to provide an extended passage for the penis 31 when the fixture is fitted thereover. The open front end 23E of condom 23 is rolled to create an elastic ring. This ring normally embraces collar 30C, and when the penis is projected through the collar and the front end 23E is unrolled, it then snugly engages the shaft of the penis.

Also the fixture shown in FIGS. 3 and 5 may be provided with a generally rectangular flange acting as a guard to shield the pubic hair surrounding the penis, and thereby avoid the need to shave this hair which otherwise would interfere with the operation of the fixture. Shield 32 is shown in dotted lines in FIG. 3.

Modified Pouches

Instead of using a standard urostomy pouch, use may be made of a similar pouch tailored to urine collection from a penis rather than from a stoma. Such a pouch, as shown in FIG. 6, may include a membrane 11A covering the upper half of the pouch inlet opening 11 surrounded by flange 12.

When flange 12 of the pouch is coupled to fixture 22 as shown in FIG. 4, the penis will then be forced downward by the membrane 11A and aimed into the pouch to facilitate urine collection.

Another way to ensure that the penis is downwardly aimed even when the user is reclining or sitting is to provide belt 17 with an extension that overlaps the pouch so as to press the penis within the pouch downwardly therein.

Still another way to facilitate urine collection is to provide a shallow pouch whose outer wall intercepts the penis projected through the inlet and bends it downward into the pouch.

While there have been shown preferred embodiments of an assembly in accordance with the invention, it will be appreciated that many changes may be made therein without departing from the essential aspects of the invention. Thus instead of using a standard urostomy pouch, use may be made of a similar pouch tailored to urine collection from a penis rather than from a stoma.

I claim:

1. A urine collecting assembly installable on an incontinent male having a penis provided with a shaft terminating in a head, said assembly comprising:

A. a normally-flat urostomy pouch formed of synthetic plastic film material having a lateral inlet adjacent its upper end bordered by a circular belt-adapter flange, and a belt of adjustable length connectable to the flange to suspend the pouch from the hips or waist of the incontinent male so that his penis then projects toward the inlet of the pouch;

B. a complementary fixture connectable to the flange which fits over the penis and has a circular opening therein whose diameter is larger than that of a male penis regardless of its size, whereby when the fixture is connected to the flange it is then joined to the inlet of the pouch; and C. a short open-ended condom having a stretchable open rear end and a stretchable open front end which is extendible along the shaft to cause the condom to snugly engage the shaft of the penis, the rear end of the condom being stretched and attached to the fixture whereby the penis on which the fixture is fitted projects through the condom into the inlet and urine discharged from the head of the penis is collected by the pouch which is dilated to accommodate the urine, thereby creating a sealing membrane which prevents backup of urine through the fixture and soiling of the incontinent male by his own urine.

2. An assembly as set forth in claim 1, in which the open, front end of the condom is normally rolled, and after the penis is projected therethrough, is then unrolled to engage the shaft of the penis.

3. An assembly as set forth in claim 1, in which the pouch is formed by two superposed plastic film plies that are peripherially bonded together to define a urine receptacle, said flange being mounted on one of these plies.

4. An assembly as set forth in claim 3, in which the pouch is provided with a drainage valve at its lower end.

5. An assembly as set forth in claim 1, in which the flange is provided with diametrically-opposed links to which are connectable connectors attached to the ends of the belt.

6. An assembly as set forth in claim 1 in which the flange is provided with an annular channel having flexible walls, and said fixture is provided with a circular ridge that snap fits into the channel.

7. An assembly as set forth in claim 1, in which the fixture is provided with an insert having a truncated conical form to support the stretched rear end of the condom.

8. An assembly as set forth in claim 7, in which the form terminates in a collar to support the front end of the condom when it is in a rolled state.

9. An assembly as set forth in claim 1, in which the fixture is provided with a guard to shield pubic hair surrounding the penis.

10. An assembly as set forth in claim 1, in which the condom is shaped to cause the penis to project downward.

11. An assembly as set forth in claim 1, in which the upper half of the circular opening in the fixture is covered by a membrane which forces the penis to project downwardly.

* * * * *